United States Patent
Hattori

(10) Patent No.: US 9,535,007 B2
(45) Date of Patent: Jan. 3, 2017

(54) MEASURING APPARATUS AND FLUORESCENCE MEASURING METHOD

(71) Applicant: OLYMPUS CORPORATION, Shibuya-ku, Tokyo (JP)

(72) Inventor: Toshiyuki Hattori, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/801,012

(22) Filed: Jul. 16, 2015

(65) Prior Publication Data

US 2016/0018332 A1 Jan. 21, 2016

(30) Foreign Application Priority Data

Jul. 18, 2014 (JP) .................................. 2014-147801

(51) Int. Cl.
*G01N 21/64* (2006.01)
*G01N 21/27* (2006.01)

(52) U.S. Cl.
CPC ........ *G01N 21/6456* (2013.01); *G01N 21/274* (2013.01); *G01N 21/6402* (2013.01); *G01N 21/6458* (2013.01); *G01N 2021/6421* (2013.01); *G01N 2021/6423* (2013.01); *G01N 2201/12707* (2013.01)

(58) Field of Classification Search
CPC ................ G01N 21/6456; G01N 21/64; G01N 2021/6421; G01N 21/6402
See application file for complete search history.

(56) References Cited

U.S. PATENT DOCUMENTS

| | | | |
|---|---|---|---|
| 5,833,617 A | 11/1998 | Hayashi | |
| 6,026,319 A | 2/2000 | Hayashi | |
| 7,986,824 B2 | 7/2011 | Suzuki et al. | |
| 8,280,142 B2 | 10/2012 | Suzuki et al. | |
| 9,052,286 B2 * | 6/2015 | Nakamura | ......... A61B 1/00009 |
| 2004/0146913 A1 | 7/2004 | Hirano et al. | |

(Continued)

FOREIGN PATENT DOCUMENTS

| | | |
|---|---|---|
| EP | 1441219 A2 | 7/2004 |
| EP | 2765406 A1 | 8/2014 |

(Continued)

OTHER PUBLICATIONS

Extended European Search Report dated Nov. 26, 2015, issued in counterpart European Application No. 15176960.1.

*Primary Examiner* — Marcus Taningco
(74) *Attorney, Agent, or Firm* — Holtz, Holtz & Volek PC

(57) ABSTRACT

A low-noise fluorescence image and a low-noise luminescence image are acquired even if a luminescent substance having a high luminescence level is used. Provided is a measuring apparatus including an illumination optical system that radiates excitation light coming from an excitation light source onto a specimen A, an image acquisition portion that acquires an image by measuring light generated at the specimen, and an image processing portion that, based on a first image, which is acquired by the image acquisition portion without radiating the excitation light, and a second image, which is acquired by the image acquisition portion while radiating the excitation light, generates a fluorescence image by removing a luminescence component from the second image.

15 Claims, 3 Drawing Sheets

(56) References Cited

U.S. PATENT DOCUMENTS

2008/0297890 A1* 12/2008 Natori .................. A61B 5/0059
359/372
2014/0227681 A1   8/2014 Fleming et al.
2014/0254953 A1   9/2014 Sato

FOREIGN PATENT DOCUMENTS

| JP | 2008128982 A  | 6/2008 |
| JP | 5123660 B2    | 1/2013 |
| WO | 2012012499 A1 | 1/2012 |
| WO | 2012083206 A1 | 6/2012 |
| WO | 2013051317 A1 | 4/2013 |

* cited by examiner

MEASURING APPARATUS AND
FLUORESCENCE MEASURING METHOD

CROSS-REFERENCE TO RELATED APPLICATIONS

This application is based on Japanese Patent Application No. 2014-147801, the contents of which are incorporated herein by reference.

TECHNICAL FIELD

The present invention relates to a measuring apparatus and a fluorescence measuring method.

BACKGROUND ART

In the related art, there are known measuring apparatuses with which both fluorescence images and luminescence images can be acquired (for example, see Patent Literature 1).

With this measuring apparatus, because the luminescence level of a luminescent substance is so weak that it is negligible as compared with the fluorescence level of a fluorescent substance, it is possible to acquire a fluorescence image regardless of the presence/absence of luminescence from the luminescent substance when measuring fluorescence.

CITATION LIST

Patent Literature

{PTL 1} Publication of Japanese Patent No. 5123660

SUMMARY OF INVENTION

Technical Problem

The present invention provides a measuring apparatus and a fluorescence measuring method with which it is possible to acquire a low-noise fluorescence image and a low-noise luminescence image even if a luminescent substance having a high luminescence level is used.

Solution to Problem

In order to achieve the above-described object, the present invention provides the following solutions.

An aspect of the present invention is a measuring apparatus including an illumination optical system that radiates excitation light coming from an excitation light source onto a specimen; an image acquisition portion that acquires an image by measuring light generated at the specimen; and an image processing portion that, based on a first image, which is acquired by the image acquisition portion without radiating the excitation light, and a second image, which is acquired by the image acquisition portion while radiating the excitation light, generates a fluorescence image by removing a luminescence component from the second image.

Another aspect of the present invention is a fluorescence measuring method including a first step of acquiring a first image by capturing an image of a specimen without radiating excitation light; a second step of acquiring a second image by capturing an image of the specimen in a state in which excitation light is radiated thereonto; and a third step of generating a fluorescence image by removing a lumines- cence component from the second image based on the first image acquired in the first step and the second image acquired in the second step.

DESCRIPTION OF EMBODIMENTS

A measuring apparatus 1 according to a first embodiment of the present invention will be described below with reference to the drawings.

Figure 1:
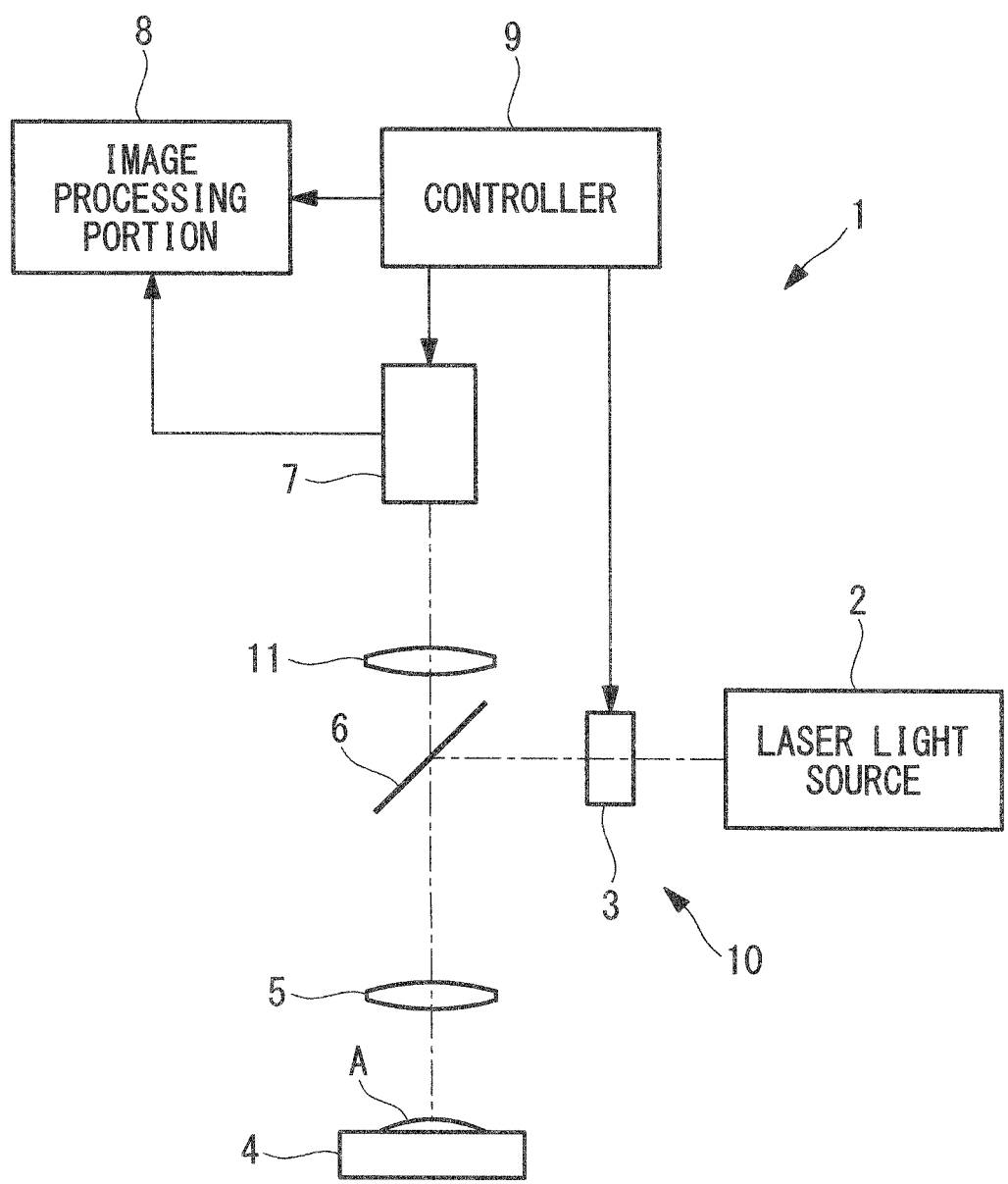
FIG. 1 is an overall configuration diagram showing a measuring apparatus according to a first embodiment the present invention.

As shown in FIG. 1, the measuring apparatus 1 according to this embodiment is a microscope provided with a laser light source (excitation light source) 2 that generates excitation light, a shutter 3 that is disposed adjacent to the laser light source 2 and that switches between the ON state and the OFF state of the excitation light coming from the laser light source 2, a stage 4 on which a specimen A is placed, and an objective lens 5 that radiates the excitation light coming from the laser light source 2 onto the specimen A on the stage 4 and that, on the other hand, collects fluorescence and luminescence generated at the specimen A.

In addition, the measuring apparatus 1 is provided with a filter 6 that splits off the fluorescence and the luminescence from the specimen A, which have been collected by the objective lens 5, from the optical path of the excitation light, a detector 7 that acquires images by detecting the fluorescence and the luminescence from the specimen A, which have been split off by the filter 6, an image processing portion 8 that processes the images acquired by the detector 7, and a controller 9 that controls the shutter 3, the detector 7, and the image processing portion 8. The shutter 3 and the objective lens 5 constitute an illumination optical system 10. In addition, reference sign 11 indicates an imaging lens.

The filter 6 is, for example, a dichroic mirror, having transmittance characteristics such that the excitation light coming from the laser light source 2 is reflected, and the fluorescence and the luminescence from the specimen A are allowed to pass therethrough.

The detector 7 is, for example, an image acquisition device such as a CCD or a CMOS device, and is configured so as to capture luminescence images or fluorescence images of the specimen A.

The controller 9 is configured so as to activate the detector 7 so that at least one image each is acquired when the shutter 3 is closed and when the shutter 3 is opened.

The image processing portion 8 receives, from the detector 7, a first image that is acquired when the shutter 3 is closed by the controller 9 and a second image that is acquired when the shutter 3 is opened by the controller 9, and generates a fluorescence image by subtracting the first image from the second image. The controller 9 and the image processing portion 8 are implemented by, for example, using a computer.

A fluorescence measuring method in which the thus-configured measuring apparatus 1 according to this embodiment is employed will be described below.

In order to acquire a luminescence image and a fluorescence image by using the measuring apparatus 1 according to this embodiment, the specimen A is placed on the stage 4, and the shutter 3 and the detector 7 are activated by operating the controller 9 in a state in which the excitation light is emitted by activating the laser light source 2.

First, the first image is acquired by capturing an image of the specimen A in a state in which the shutter 3 is closed by the controller 9 (first step S1).

In the state in which the shutter 3 is closed, because the excitation light is not radiated onto the specimen A, only luminescence from a luminescent substance is generated at the specimen A. The luminescence emitted from the specimen A is collected by the objective lens 5, passes through the filter 6, and is captured by the detector 7. Accordingly, the first image acquired by the detector 7 is a luminescence image that does not include fluorescence, and is transmitted to the image processing portion 8.

Next, the second image is acquired by capturing an image of the specimen A in a state in which the shutter 3 is opened by the controller 9 (second step S2).

In the state in which the shutter 3 is opened, the excitation light emitted from the laser light source 2 is deflected at the filter 6, is focused by the objective lens 5, and is radiated onto the specimen A on the stage 4. At the specimen A, a fluorescent substance is excited by the excitation light, generating fluorescence, and the luminescence from the luminescent substance is also generated regardless of the presence/absence of the excitation light.

The fluorescence and the luminescence emitted from the specimen A are collected by the objective lens 5, pass through the filter 6, and are captured by the detector 7. Accordingly, the second image acquired by the detector 7 is a luminescence/fluorescence image that includes the fluorescence and the luminescence, and is transmitted to the image processing portion 8.

When the first image and the second image are transmitted thereto from the detector 7, the image processing portion 8 follows an instruction from the controller 9 and performs processing in which the first image is subtracted from the second image (third step S3). Because the luminescence component included in the first image and the luminescence component included in the second image are identical, by subtracting the first image from the second image, the fluorescence image can be generated by removing the luminescence component included in the second image. Note that the first image itself is a luminescence image in this embodiment.

As has been described above, with the measuring apparatus 1 and the fluorescence measuring method according to this embodiment, because the luminescence component included in the second image is removed, there is an advantage in that it is possible to acquire a low-noise fluorescence image even if a luminescent substance having a high luminescence level is used. In addition, because fluorescence is not included in the luminescence image obtained by blocking the excitation light with the shutter 3, it is also possible to acquire a low-noise luminescence image at the same time.

Next, a measuring apparatus 20 according to a second embodiment of the present invention will be described below with reference to the drawings.

In describing this embodiment, the same reference signs will be assigned to portions that have the same configurations as those of the measuring apparatus 1 according to the first embodiment described above, and descriptions thereof will be omitted.

Figure 2:
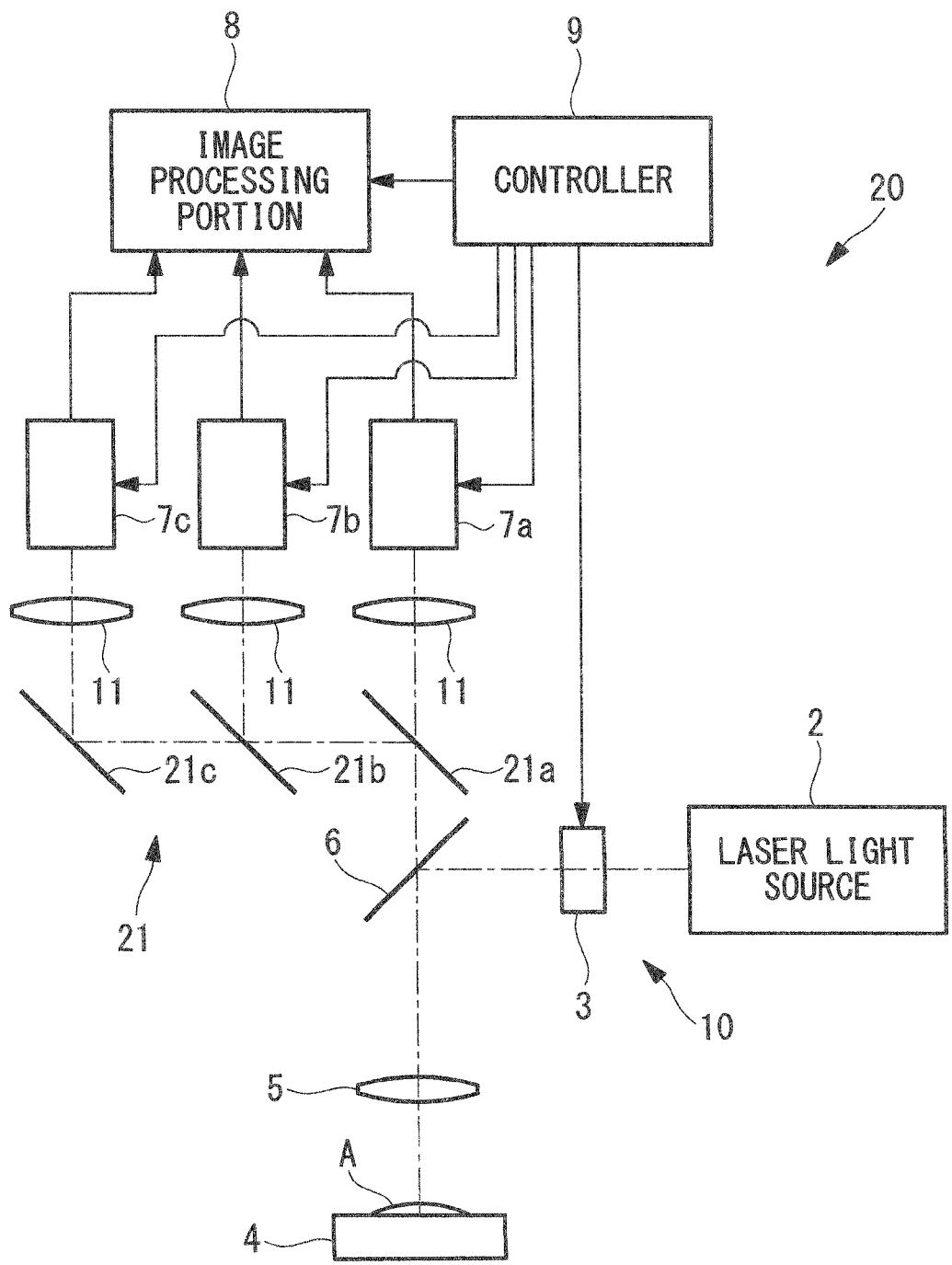
FIG. 2 is an overall configuration diagram showing a measuring apparatus according to a second embodiment of the present invention.

As shown in FIG. 2, the measuring apparatus 20 according to this embodiment employs, as a filter, a spectral portion 21 that disperses the fluorescence and the luminescence emitted from the specimen A into a plurality of wavelength bands. The spectral portion 21 is provided with, for example, three dichroic mirrors 6, 21a, and 21b and a mirror 21c that have different transmittance characteristics, and is configured so as to disperse the fluorescence and the luminescence emitted from the specimen A into three different wavelength bands by means of the dichroic mirrors 21a and 21b and the mirror 21c, after the fluorescence and the luminescence emitted from the specimen A are split off from the optical path of the excitation light by means of the dichroic mirror 6.

In addition, the measuring apparatus 20 according to this embodiment is provided with three detectors 7a to 7c that individually detect the fluorescence and the luminescence that have been split into three wavelength bands by the spectral portion 21. Images separately acquired by the three detectors 7a to 7c in accordance with the wavelengths are transmitted to the image processing portion 8 to be subjected to image processing.

In this embodiment, the image processing portion 8 performs image processing described below.

The image processing portion 8 generates spectra based on the images transmitted thereto from the detectors 7a to 7c, and applies known unmixing processing to the luminescence/fluorescence image based on the generated spectra.

More specifically, first, first images are acquired by capturing images of the specimen A in the state in which the shutter 3 is closed by the controller 9 (first step S1).

In the state in which the shutter 3 is closed, because the excitation light is not radiated onto the specimen A, only luminescence from a luminescent substance is generated at the specimen A.

The luminescence emitted from the specimen A is collected by the objective lens 5, is separated into three different wavelength bands by the spectral portion 21, and the respective luminescence components are captured by the three separate detectors 7a to 7c. Accordingly, the three first images acquired by the detectors 7a to 7c are three types of luminescence images that do not include fluorescence and that are of different wavelength bands, and are transmitted to the image processing portion 8.

Next, second images are acquired by capturing images of the specimen A in a state in which the shutter 3 is opened by the controller 9 (second step S2).

In the state in which the shutter 3 is opened, the excitation light emitted from the laser light source 2 is focused by the objective lens 5, and is radiated onto the specimen A on the stage 4. At the specimen A, a fluorescent substance is excited by the excitation light, generating fluorescence, and the luminescence from the luminescent substance is also generated regardless of the presence/absence of the excitation light.

The fluorescence and the luminescence emitted from the specimen A are collected by the objective lens 5, are separated into the three different wavelength bands by the spectral portion 21, and the respective fluorescence components and luminescence components are captured by the three separate detectors 7a to 7c. Accordingly, the three second images acquired by the detectors 7a to 7c are luminescence/fluorescence images that include the fluorescence and the luminescence, and are transmitted to the image processing portion 8.

When the first images and the second images are transmitted thereto from the detectors 7a to 7c, the image processing portion 8 follows an instruction from the controller 9 and performs image processing (third step S3). First of all, the image processing portion 8 generates luminescence spectra X from the three first images, and generates luminescence/fluorescence spectra Z for each pixel based on the three second images.

Subsequently, the image processing portion 8 performs unmixing processing assuming that the generated emitted-light spectra X, luminescence/fluorescence spectra Z, and known fluorescence spectra Y satisfy the relational expression below, and calculates the unknown coefficients α and β for each pixel.

$$\alpha X + \beta Y = Z$$

Note that, for the known fluorescence spectra Y, measurements are taken in advance by using a sample including only fluorescence or spectra of a portion emitting only fluorescence are used.

Then, the image processing portion 8 uses the calculated coefficients α and β to calculate fluorescence signals included in the individual pixel signals, and thus, generates the fluorescence image.

Specifically, because the ratio between the luminescence spectra X and the fluorescence spectra Y included in the luminescence/fluorescence spectra Z is determined by calculating the coefficients α and β, it is possible to generate a fluorescence image from which the luminescence component has been removed. By doing so, there is an advantage in that it is possible to generate a fluorescence image from which the luminescence component has been removed even when the fluorescence component and the luminescence component are spatially overlapping.

Note that, although this embodiment has been described assuming that the specimen A contains a single type of luminescent substance and a single type of fluorescent substance, alternatively, the present invention may be applied to the case in which the specimen A contains multiple types of luminescent substances and/or multiple types of fluorescent substances.

In this case, emitted-light spectra need to be generated for the respective luminescent substances and/or fluorescence spectra need to be generated for the respective fluorescent substances.

For example, by identifying pixels from which only luminescence from the respective luminescent substances are acquired, and by plotting wavelength distributions of luminances of the luminescence for these pixels, emitted-light spectra $X_1$ to $X_n$ can be generated in a simple manner. In addition, by identifying pixels from which only fluorescence from the respective fluorescent substances are acquired, and by plotting wavelength distributions of luminances of the fluorescence for these pixels, fluorescence spectra $Y_1$ to $Y_n$ can be generated in a simple manner.

Therefore, by performing unmixing processing by using the expression below, it is possible to calculate coefficients $\alpha_1$ to $\alpha_n$ and $\beta_1$ to $\beta_n$ that express mixing ratios between the emitted-light spectra $X_1$ to $X_n$ and the fluorescence spectra $Y_1$ to $Y_n$ for each pixel, and it is possible to generate a fluorescence image from which the luminescence component has been removed based on the calculated coefficients $\alpha_1$ to $\alpha_n$ and $\beta_1$ to $\beta_n$.

$$\alpha_1 X_1 + \alpha_2 X_2 + \ldots + \alpha_n X_n + \beta_1 Y_1 + \beta_2 Y_2 + \ldots + \beta_n Y_n = Z$$

Here, $\alpha_1$ to $\alpha_n$ and $\beta_1$ to $\beta_n$ are unknown coefficients.

Figure 3:
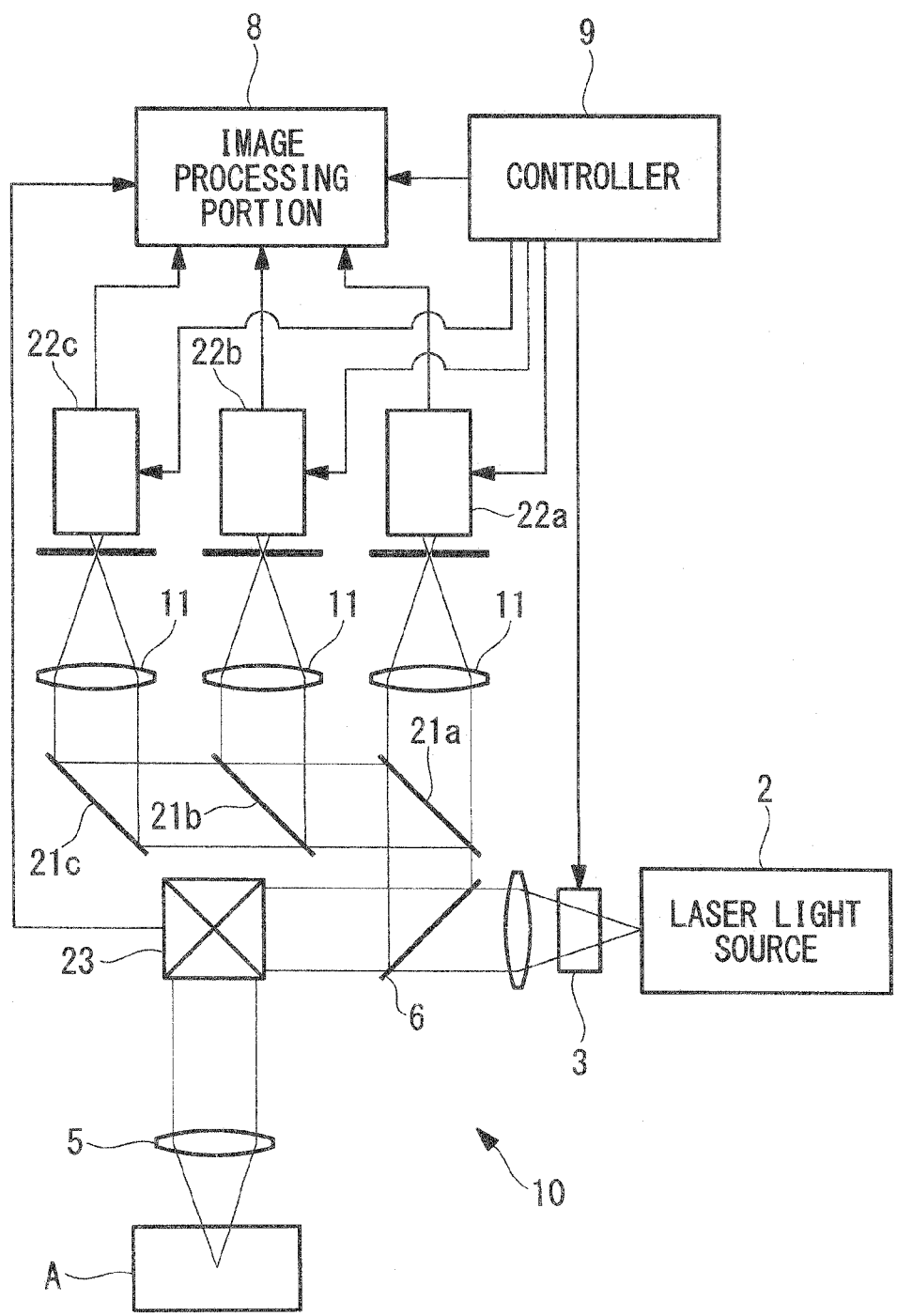
FIG. 3 is an overall configuration diagram showing a modification of the measuring apparatus according to the embodiment in FIG. 2.

In addition, although cases in which image acquisition devices are employed as the detectors 7a to 7c have been described in the individual embodiments described above, alternatively, as shown in FIG. 3, by employing photo-detectors 22a to 22c such as photomultiplier tubes, the present invention may be applied to a scanning confocal microscope provided with a scanner 23 that two-dimensionally scans light coming from the laser light source 2. In this case, the fluorescence image and the luminescence/fluorescence image may be generated by associating, in the image processing portion 8, positions at which the excitation light is scanned by the scanner 23 and intensities of the fluorescence and the luminescence detected by the photo-detectors 22a to 22c. In order to acquire the luminescence image, intensities of the luminescence from the specimen A should be associated with the scanning positions of the scanner 23 by using so-called blank scanning in which the scanner 23 is driven without radiating the excitation light by closing the shutter 3.

In addition, in this embodiment, although the luminescence image is acquired in the state in which the excitation light coming from the laser light source 2 is blocked by closing the shutter 3 before acquiring the luminescence/fluorescence image, in the case in which a fluorescence image is extracted from the luminescence/fluorescence image by means of the unmixing processing, the shutter 3 need not be provided. Specifically, because it is possible to acquire the luminescence spectra of the luminescent substance without having to radiate the excitation light in advance, by storing luminescence spectra acquired in this way, the unmixing processing may be performed by using the stored luminescence spectra when separating the fluorescence spectra from the luminescence/fluorescence spectra acquired by radiating the excitation light.

In addition, although an example in which the spectral portion 21 is formed of a plurality of dichroic mirrors 21a and 21b, and so forth has been described, alternatively, a spectral portion provided with a diffraction grating and a movable slit or a spectral portion employing a system in which filters are switched may be employed.

With the measuring apparatus according to this embodiment, by radiating the excitation light emitted from the excitation light source onto the specimen by using the illumination optical system, fluorescence is generated at the specimen due to the excitation of a fluorescent substance contained therein. In the case in which the specimen contains a luminescent substance, luminescence is generated from the luminescent substance regardless of the presence/absence of irradiation with the excitation light. Therefore, the first image acquired by the image acquisition portion without radiating the excitation light includes only the luminescence component, and the second image acquired by the image acquisition portion by radiating the excitation light includes both the luminescence component and the fluorescence component. Therefore, with the first image, it is possible acquire a luminescence image that does not include fluorescence, and, by generating the fluorescence image by removing the luminescence component from the second image at the image processing portion based on the first image and the second image, it is possible to acquire a low-noise fluorescence image even if a luminescent substance having a high luminescence level is used.

In the above-described measuring apparatus, the image acquisition portion may be provided with a spectral portion that disperses light generated at the specimen.

By doing so, the first image and the second image can be acquired in the forms of images in which the light generated at the specimen is dispersed by the spectral portion in accordance with the wavelengths. By doing so, it is possible to remove the luminescence component from the second image in accordance with the wavelengths based on the dispersed light images.

In the above-described measuring apparatus, the image processing portion may subtract the first image from the second image.

By doing so, by subtracting the first image, which includes only the luminescence component, from the second image, which includes the luminescence component and the fluorescence component, it is possible to generate, in a simple manner, the fluorescence image from which the luminescence component has been removed.

In the above-described measuring apparatus, the image processing portion may perform unmixing processing based on the first image and the second image.

By doing so, spectra that are only for the luminescence component are obtained from the first image, which is acquired by dispersing the light generated at the specimen without radiating the excitation light thereonto, spectra that include both the fluorescence component and the luminescence component are also obtained from the second image, which is acquired by dispersing the light generated at the specimen by radiating the excitation light thereonto, and, by performing the unmixing processing based on these spectra, it is possible to separate the fluorescence component and the luminescence component and to obtain the fluorescence image from which the luminescence component has been removed.

In the above-described measuring apparatus, the illumination optical system may be provided with a shutter that blocks the excitation light, an image acquired by the image acquisition portion in a state in which the excitation light is blocked by closing the shutter may be assumed to be the first image, and an image acquired by the image acquisition portion in a state in which the excitation light is radiated by opening the shutter may be assumed to be the second image.

By doing so, it is possible to acquire the first image and the second image in a simple manner by switching between the two by opening and closing the shutter.

In the above-described fluorescence measuring method, in the first step, the first image may be acquired by dispersing light generated at the specimen, and, in the second step, the second image may be acquired by dispersing the light generated at the specimen.

In the above-described fluorescence measuring method, in the third step, the first image may be subtracted from the second image.

In the above-described fluorescence measuring method, in the third step, unmixing processing may be performed based on the first image and the second image.

REFERENCE SIGNS LIST

A specimen
1, 20 measuring apparatus
2 laser light source (excitation light source)
3 shutter
7, 7a, 7b, 7c detector (image acquisition portion)
8 image processing portion
10 illumination optical system
21 spectral portion
22a, 22b, 22c photo-detector (image acquisition portion)
23 scanner (image acquisition portion)

The invention claimed is:

1. A measuring apparatus comprising:
    an illumination optical system that radiates excitation light coming from an excitation light source onto a specimen;
    an image acquisition portion that acquires an image by measuring light generated at the specimen; and
    an image processing portion that, based on a first image, which is acquired by the image acquisition portion without radiating the excitation light, and a second image, which is acquired by the image acquisition portion while radiating the excitation light, generates a fluorescence image by removing a luminescence component from the second image,
    wherein the first image is a luminescence image including only the luminescence component from a luminescent substance included in the specimen, and
    wherein the second image is a luminescence and fluorescence image including both the luminescence component and a fluorescence component.

2. A measuring apparatus according to claim 1, wherein the image acquisition portion is provided with a spectral portion that disperses the light generated at the specimen.

3. A measuring apparatus according to claim 1, wherein the image processing portion subtracts the first image from the second image.

4. A measuring apparatus according to claim 1, wherein the illumination optical system is provided with a shutter that blocks the excitation light, and wherein an image acquired by the image acquisition portion in a state in which the excitation light is blocked by closing the shutter is the first image, and an image acquired by the image acquisition portion in a state in which the excitation light is radiated by opening the shutter is the second image.

5. A measuring apparatus according to claim 2, wherein the image acquisition portion is provided with the spectral portion that is provided with at least one dichroic mirror, or the spectral portion that is provided with a diffraction grating, or the spectral portion that is employing a system in which filters are switched.

6. A measuring apparatus according to claim 2, wherein the image processing portion performs unmixing processing based on the first image and the second image.

7. A measuring apparatus according claim 6, wherein the unmixing processing comprises:
    generating a wavelength spectrum X of the luminescence component from the first image that does not include the fluorescence component acquired via the spectral portion;
    generating a wavelength spectrum Z of the luminescence component and the fluorescence component from the second image acquired via the spectral portion; and
    generating the fluorescence image based on at least one of coefficients α and β that are calculated for each pixel using the following expression:

$\alpha X + \beta Y = Z$, where Y indicates a wavelength spectrum of a fluorescence that a fluorescent substance included in the specimen emits.

8. A measuring apparatus according claim 6, wherein the unmixing processing comprises:
    generating emitted-light spectra $X_1$ to $X_n$ based on pixels from which only luminescence from respective luminescent substances are acquired;

generating fluorescence spectra $Y_1$ to $Y_n$ based on pixels from which only fluorescence from respective fluorescent substances are acquired;

generating a wavelength spectrum Z of the luminescence component and the fluorescence component from the second image acquired via the spectral portion; and generating the fluorescence image based on either coefficients $\alpha_1$ to $\alpha_n$ or coefficients $\beta_1$ to $\beta_n$, or both that are calculated for each pixel using the following expression:

$$\alpha_1 X_1 + \alpha_2 X_2 + \ldots + \alpha_n X_n + \beta_1 Y_1 + \beta_2 Y_2 + \ldots + \beta_n Y_n = Z.$$

9. A fluorescence measuring method comprising:
acquiring a first image by capturing an image of a specimen without radiating excitation light onto the specimen;

acquiring a second image by capturing an image of the specimen in a state in which the excitation light is radiated onto the specimen; and generating a fluorescence image by removing a luminescence component from the second image based on the acquired first image and the acquired second image, wherein the first image is a luminescence image including only the luminescence component from a luminescent substance included in the specimen, and wherein the second image is a luminescence and fluorescence image including both the luminescence component and a fluorescence component.

10. A fluorescence measuring method according to claim 9, wherein the first and second images are acquired by dispersing light generated at the specimen.

11. A fluorescence measuring method according to claim 9, wherein the fluorescence image is generated by subtracting the first image from the second image.

12. A fluorescence measuring method according to claim 10, wherein the light is dispersed by at least one of a dichroic mirror, a diffraction grating, and a filter.

13. A fluorescence measuring method according to claim 10, wherein the fluorescence image is generated by performing unmixing processing based on the first image and the second image.

14. A fluorescence measuring method according to claim 13, wherein the unmixing processing comprises:
generating a wavelength spectrum X of the luminescence component from the first image that does not include the fluorescence component acquired via a spectral portion;

generating a wavelength spectrum Z of the luminescence component and the fluorescence component from the second image acquired via the spectral portion; and generating the fluorescence image based on at least one of coefficients $\alpha$ and $\beta$ that are calculated for each pixel using the following expression:

$$\alpha X + \beta Y = Z,$$

where Y indicates a wavelength spectrum of a fluorescence that a fluorescent substance included in the specimen emits.

15. A fluorescence measuring method according to claim 13, wherein the unmixing processing comprises:
generating emitted-light spectra $X_1$ to $X_n$ based on pixels from which only luminescence from respective luminescent substances are acquired;

generating fluorescence spectra $Y_1$ to $Y_n$ based on pixels from which only fluorescence from respective fluorescent substances are acquired;

generating a wavelength spectrum Z of the luminescence component and the fluorescence component from the second image acquired via a spectral portion; and generating the fluorescence image based on either coefficients $\alpha_1$ to $\alpha_n$ or coefficients $\beta_1$ to $\beta_n$, or both that are calculated for each pixel using the following expression:

$$\alpha_1 X_1 + \alpha_2 X_2 + \ldots + \alpha_n X_n + \beta_1 Y_1 + \beta_2 Y_2 + \ldots + \beta_n Y_n = Z.$$

* * * * *